(12) United States Patent
Bassler et al.

(10) Patent No.: US 7,408,073 B2
(45) Date of Patent: Aug. 5, 2008

(54) RETURNING AN OLEFIN WHICH IS NOT REACTED DURING THE OXIDATION OF OLEFINS

(75) Inventors: Peter Bassler, Viernheim (DE); Hans-Georg Goebbel, Kallstadt (DE); Joaquim Henrique Teles, Otterstadt (DE); Peter Rudolf, Ladenburg (DE)

(73) Assignee: BASF Aktiengesellschaft, Ludwigshafen (DE)

(*) Notice: Subject to any disclaimer, the term of this patent is extended or adjusted under 35 U.S.C. 154(b) by 411 days.

(21) Appl. No.: 10/532,096

(22) PCT Filed: Oct. 23, 2003

(86) PCT No.: PCT/EP03/11736

§ 371 (c)(1), (2), (4) Date: Apr. 21, 2005

(87) PCT Pub. No.: WO2004/037802

PCT Pub. Date: May 6, 2004

(65) Prior Publication Data

US 2006/0058539 A1    Mar. 16, 2006

(30) Foreign Application Priority Data

Oct. 23, 2002   (DE) ................ 102 49 378

(51) Int. Cl.
*C07D 301/12*   (2006.01)
(52) U.S. Cl. .................................... 549/531
(58) Field of Classification Search .......... 549/524, 549/529, 531
See application file for complete search history.

(56) References Cited

U.S. PATENT DOCUMENTS 3,000,188 A * 9/1961 Greco ................ 62/620

FOREIGN PATENT DOCUMENTS

| DE | 101 55 470 | | 5/2003 |
|---|---|---|---|
| EP | 0 467 538 | | 1/1992 |
| EP | 0 646 558 | | 4/1995 |
| EP | 0 719 768 | | 7/1996 |
| WO | 00/07965 | | 2/2000 |
| WO | 02/14298 | | 2/2002 |
| WO | WO 02/14298 | * | 2/2002 |

OTHER PUBLICATIONS

Ullmann's Encyclopedia of Industrial Chemistry, vol. A22, p. 214.

* cited by examiner

*Primary Examiner*—Bernard Dentz
*Assistant Examiner*—David E Gallis
(74) *Attorney, Agent, or Firm*—Oblon, Spivak, McClelland, Maier & Neustadt, P.C.

(57) ABSTRACT

Process for the continuous recirculation of the olefin which has not been reacted in the epoxidation of olefins by means of hydroperoxide to give oxiranes and is present in the offgas stream formed during the epoxidation, which comprises the steps (i) to (iii)

(i) compressing and cooling the offgas stream,
(ii) seperating the olefin from the offgas stream obtain in step (i) by distillation,
(iii) epoxidizing the olefin seperating off in step (ii) by means of hydroperoxide.

29 Claims, 1 Drawing Sheet

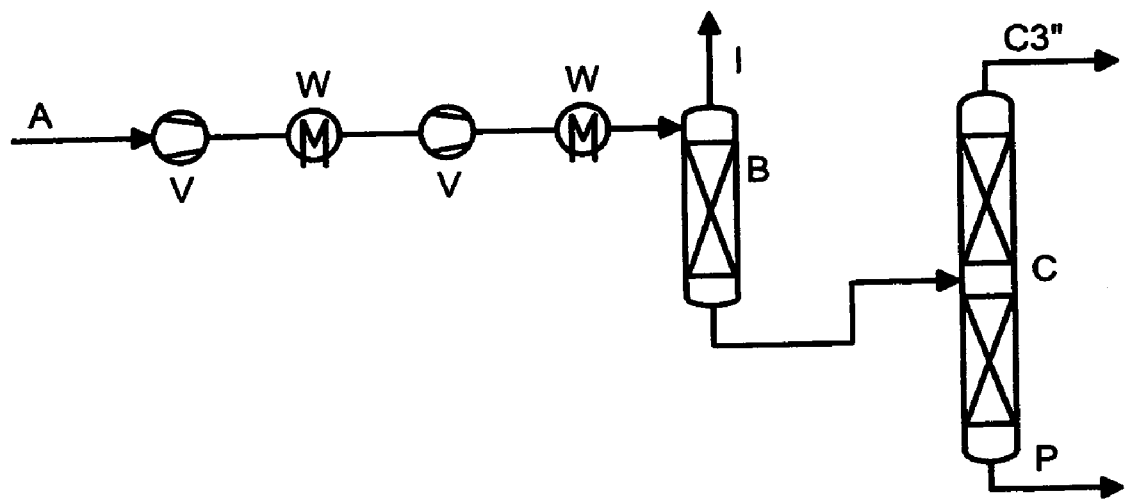

RETURNING AN OLEFIN WHICH IS NOT REACTED DURING THE OXIDATION OF OLEFINS

The invention relates to a process for the continuous recirculation of the olefin which has not been reacted in the epoxidation of olefins by means of hydroperoxides to give oxiranes. In this process, the offgas stream formed in the epoxidation is compressed with cooling and separated in a pressure distillation into an olefin-containing bottom stream and an offgas stream which is largely free of hydrocarbons. The olefin is recirculated to the epoxidation process. The process can be employed particularly advantageously for the recirculation of the propene used in the preparation of propene oxide. The invention also relates to an apparatus by means of which the process can be carried out.

It is known that in the epoxidation of olefins by means of hydroperoxides to give oxiranes, the selectivity of oxirane formation decreases significantly and the level of undesirable secondary reactions increases as the olefin conversion rises. To be able to achieve a high selectivity of over 95% despite this, these reactions are, especially on an industrial scale, therefore preferably carried out only to an olefin conversion of about 85 to 95%.

Isolating the unreacted olefin from the reaction process and then recirculating it to the oxidation process (epoxidation) is also known. Thus, a process in which a gas mixture comprising the olefin and oxygen originating from the decomposition reaction of the hydrogen peroxide used as hydroperoxide in the epoxidation is separated off and the olefin is absorbed from the gas mixture in a liquid absorption medium has been proposed. In this process, a sufficient amount of an inert gas has to be added to the oxygen to prevent formation of flammable gas compositions. In a preferred embodiment, this process is used for recovering propene from the reaction of propene with hydrogen peroxide to give propene oxide. The inert gas used is preferably methane and the liquid absorption medium used is preferably a mixture comprising isopropanol and water (EP-B 0 719 768).

In this process, the low solubility of the olefin in water-containing isopropanol has an unfavorable effect. For this reason, relatively large amounts of solvent have to be used in order to be able to recover the olefin from the offgas stream by absorption. Furthermore, feeding a further gas, in particular methane, in addition to the offgas stream to the column used for the absorption is uneconomical.

It is an object of the present invention to provide an improved process for recovering the olefin used in the epoxidation of olefins to oxiranes, by means of which it is possible to achieve more effective recovery of the olefin from the offgas stream than in the process of the prior art.

We have found that this object is achieved by compressing, with cooling, the offgas stream formed in the epoxidation of an olefin by means of hydroperoxide to give the oxirane, isolating the olefin present from the offgas stream by distillation and recirculating it to the epoxidation process.

The present invention accordingly provides a process for the continuous recirculation of the olefin which has not been reacted in the epoxidation of olefins by means of hydroperoxide to give oxiranes and is present in the offgas stream formed during the epoxidation, which comprises the steps (i) to (iii)

(i) compressing and cooling the offgas stream,
(ii) separating the olefin from the offgas stream obtained in step (i) by distillation,
(iii) epoxidizing the olefin separated off in step (ii) by means of hydroperoxide.

In the process of the present invention, it is not necessary to feed an inert gas into the separation apparatus in the olefin separation step in order to avoid explosive mixtures. The isolation of the olefin via an absorption plant is dispensed with. Moreover, the process of the present invention makes it possible to separate the olefin from the offgas stream in high yield at relatively low cost using a single distillation. Since the process can be operated continuously, it is especially advantageous for industrial use.

According to the prior art, the epoxidation of olefins using hydroperoxide can be carried out in one or more stages. Such methods and also an industrial process are described, for example, in WO 00/07965.

To separate off the oxiranes formed in the oxidation, it is possible to use, for example, distillation columns. Here, offgas streams are obtained at the top of the columns. These offgas streams always comprise unreacted olefin and a small amount of oxygen which originates from the decomposition reaction of the hydroperoxide used. To obtain better regulation of the distillation, it is customary to use inert gases, preferably nitrogen. Since these are likewise taken off at the top of the columns, the offgas streams further comprise these gases. It is therefore no longer necessary to feed an additional gas into the absorption plant to avoid explosive mixtures in the process of the present invention.

It is generally sufficient to cool the offgas stream to preferably from 0 to 70° C., more preferably from 15 to 55° C., in particular from 30 to 40° C., in step (i).

These temperature ranges can, for example, be established using only water as coolant.

Compression can be carried out using the customary apparatuses, for example piston compressors, diaphragm compressors, screw compressors and rotary compressors.

Compression is preferably carried out not in one stage but in a plurality of stages with cooling between the individual compression stages. This procedure has the advantage of the final compression temperature being able to be readily kept within the permissible range.

In a preferred embodiment of the process, compression of the offgas stream is carried out in two stages.

After compression, the offgas stream is then preferably under a pressure of from 2 to 30 bar, more preferably from 10 to 25 bar, in particular from 12 to 20 bar. In one embodiment of the process of the present invention, the offgas stream is accordingly cooled to from 0 to 70° C. and compressed to a pressure of from 2 to 30 bar in step (i).

The offgas stream which has been pre-treated by cooling and compression is then fed to a distillation column, which may be of a conventional type. Such columns are, for example, rectification columns preferably having from 3 to 20, more preferably from 5 to 10, theoretical plates. They can, for example, be configured as packed columns containing random or ordered packing, as tray columns or as columns having rotating internals.

The compressed offgas stream is fed continuously into the column. The feed point can be in the middle region of the column. Depending on the physical properties of the mixture to be separated, pressure and temperature are selected, for instance in the ranges described above, so that partial vaporization of the mixture to be separated occurs. The olefin can be taken off as high-boiling component of the offgas stream at the bottom of the column and the low-boiling components, for example the inert gases or further volatile by-products formed in the reaction present in the offgas stream, can be distilled off via the top of the column.

As a result of the proportion of inert gases present in the offgas stream, the separation proceeds outside the range in which explosive mixtures with oxygen can be formed. For this reason, additional introduction of further gases in the distillation step (ii) in order to prevent the formation of explosive mixtures becomes superfluous.

The gases originally present in the offgas stream which are obtained together with the low boilers can, for example, be passed to combustion.

The olefin obtained at the bottom of the column is preferably obtained in a purity of at least 90%. It can generally be fed without further purification steps to the epoxidation by means of hydroperoxide.

In the process of the present invention, it is particularly advantageous that the olefin can be recirculated to the epoxidation process in that amount in which it is separated off from the offgas stream from the epoxidation. This makes possible a continuously operated process, which is extremely economical.

The process of the present invention can be carried out particularly advantageously for the separation of propene from an offgas stream originating from the oxidation of propene to propene oxide.

As has been mentioned above, the offgas stream then comprises the propene together with inert gases, in particular nitrogen, and a small amount of oxygen.

In the epoxidation of propene to propene oxide, it is not necessary to use propene in high-purity form but it is instead possible to use "chemical grade" propene. Such propene contains propane, with the volume ratio of propene to propane being from about 97:3 to 95:5.

In a particularly preferred embodiment of the process of the present invention, the offgas stream therefore comprises propene from the epoxidation of propene to propane oxide as olefin and propane.

In this embodiment of the process of the present invention, the offgas stream is preferably cooled to from 30° C. to 40° C. and compressed to a pressure of from 12 to 20 bar. A temperature of about 35° C. and a pressure of about 16 bar are particularly preferred.

This compressed offgas stream is then fed into a distillation column, preferably at a point close to the uppermost theoretical plate, for the purposes of the separation in step (ii). Choice of such a preferred feed point leads to the column being operated-virtually as a pure stripping column. As a result, the vaporizing gas mixture within the column is enriched only relatively slightly with the high-boiling components.

This results in rapid and good isolation of the hydrocarbon-containing fraction comprising propene and propane as bottom product, while the inert gases or further volatile by-products formed in the epoxidation present in the offgas stream distil off as low-boiling fraction at the top of the column. At least 93% of the hydrocarbons can be separated off from the offgas stream. The low-boiling fraction thus contains only low concentrations of hydrocarbons, preferably less than 7% by weight of the total components present in the low-boiling fraction.

The stream comprising the components propene and propane which is obtained via the bottom of the column can subsequently be separated into the components propene and propane in a $C_3$ splitter as described, for example, in Ullmann's Encyclopedia of Industrial Chemistry, Vol. A22, page 214. The separation can be carried out in a column at a pressure of from about 15 to 25 bar. The separation can also be carried out in a $C_3$ splitter in the form of thermally coupled columns. These can, for example, be operated at a pressure of about 15 or 25 bar. The propene is obtained at the top while the propane is obtained at the bottom.

The propene can then be returned to the epoxidation by means of hydroperoxide. Propane can be used as energy source for steam generation.

Examples of olefins which can be separated off by means of the process of the present invention from offgas streams which are formed in the epoxidation of these olefins by means of hydroperoxide to give the corresponding oxiranes are the following compounds:

ethene, propene, 1-butene, 2-butene, isobutene, butadiene, pentenes, piperylene, hexenes, hexadienes, heptenes, octenes, diisobutene, trimethylpentene, nonenes, dodecene, tridecene, tetradecane to eicosene, tripropene and tetrapropene, polybutadienes, polyisobutenes, isoprene, terpenes, geraniol, linalool, linalyl acetate, methylenecyclopropane, cyclopentene, cyclohexene, norbornene, cycloheptene, vinylcyclohexane, vinyloxirane, vinylcyclohexene, styrene, cyclooctene, cyclooctadiene, vinylnorbornene, indene, tetrahydroindene, methylstyrene, dicyclopentadiene, divinylbenzene, cyclododecene, cyclododecatriene, stilbene, diphenylbutadiene, vitamin A, beta-carotene, vinylidene fluoride, allyl halides, crotyl chloride, methallyl chloride, dichlorobutene, allyl alcohol, methallyl alcohol, butenols, butenediols, cyclopentenediols, pentenols, octadienols, tridecenols, unsaturated steroids, ethoxyethene, isoeugenol, anethole, unsaturated carboxylic acids such as acrylic acid, methacrylic acid, crotonic acid, maleic acid, vinyl acetic acid, unsaturated fatty acids such as oleic acid, linoleic acid, palmitic acid, naturally occurring fats and oils.

Preference is given to using olefins which are gaseous under normal conditions or have a boiling point below 150° C. in the process of the present invention. These are preferably olefins having from 2 to 8 carbon atoms. Particular preference is given to using ethene, propene and butene. The use of propene is most preferred.

Hydroperoxides which can be used for the epoxidation are all the hydroperoxides which are known from the prior art and are suitable for reaction with the olefin. Examples of such hydroperoxides are tert-butyl hydroperoxide and ethylbenzene hydroperoxide. Hydrogen peroxide can also be used as hydroperoxide, for example as an aqueous solution.

The offgas streams can also originate from oxidation processes in which the reaction of the olefin with the hydroperoxide is catalyzed, for example by means of heterogeneous catalysts.

In a particularly preferred embodiment of the process of the present invention, propene is separated off from an offgas stream obtained in the heterogeneously catalyzed epoxidation of propene by means of hydrogen peroxide to give propene oxide.

The invention also provides an apparatus for carrying out the process of the present invention, which comprises at least one reactor for preparing propene oxide, at least one apparatus for compressing the offgas stream, at least one distillation column for separating propene and propane from the offgas stream and a $C_3$ splitter for separating propene and propane.

The flow diagram shown in the figure indicates how propene can be recovered from the epoxidation (oxidation) of propene to propene oxide by the process of the present invention, with compression being carried out in two stages with intermediate cooling.

LIST OF REFERENCE NUMERALS FOR THE FIGURE

A offgas from epoxidation
V compressor
W heat exchanger
I inert gases ($n_2$), $O_2$
B distillation column
C C3 splitter
P propane and possibly further high boilers
c3" "chemical grade" propene

We claim:
1. A process for the continuous recirculation of an olefin which has not been reacted in the epoxidation of olefins by means of hydroperoxide to give oxiranes and is present in an offgas stream formed during the epoxidation, comprising:
(i) compressing and cooling the offgas stream,
(ii) separating the olefin from the offgas stream obtained in step (i) by distillation,
(iii) epoxidizing the olefin separated off in step (ii) by means of hydroperoxide, wherein the offgas stream comprises unreacted olefin and oxygen.

2. The process as claimed in claim 1, wherein the offgas stream further comprises nitrogen.

3. The process as claimed in claim 1, wherein, in step (i), the offgas stream is compressed to a pressure of from 2 to 30 bar and cooled to from 0 to 70° C.

4. The process as claimed in claim 1, wherein compression occurs in at least two stages in step (i).

5. The process as claimed in claim 3, wherein compression occurs in at least two stages in step (i).

6. The process as claimed in claim 1, wherein the olefin is propene and the offgas stream further comprises propane.

7. The process as claimed in claim 2, wherein, in step (i), the offgas stream is compressed to a pressure of from 2 to 30 bar and cooled to from 0 to 70° C.

8. The process as claimed in claim 2, wherein compression occurs in at least two stages in step (i).

9. The process as claimed in claim 7, wherein compression occurs in at least two stages in step (i).

10. The process as claimed in claim 2, wherein the olefin is propene and the offgas stream further comprises propane.

11. The process as claimed in claim 3, wherein the olefin is propene and the offgas stream further comprises propane.

12. The process as claimed in claim 4, wherein the olefin is propene and the offgas stream further comprises propane.

13. The process as claimed in claim 3, wherein, in step (i), the offgas stream is cooled to from 30 to 40° C. and compressed to a pressure of from 12 to 20 bar.

14. The process as claimed in claim 11, wherein, in step (i), the offgas stream is cooled to from 30 to 40° C. and compressed to a pressure of from 12 to 20 bar.

15. The process as claimed in claim 7, wherein the olefin is propene and the offgas stream further comprises propane.

16. The process as claimed in claim 8, wherein the olefin is propene and the offgas stream further comprises propane.

17. The process as claimed in claim 7, wherein, in step (i), the offgas stream is cooled to from 30 to 40° C. and compressed to a pressure of from 12 to 20 bar.

18. The process as claimed in claim 15, wherein, in step (i), the offgas stream is cooled to from 30 to 40° C. and compressed to a pressure of from 12 to 20 bar.

19. The process as claimed in claim 6, wherein a mixture of propene and propane obtained in the bottoms from a column after the distillation in step (ii) is separated into propene and propane in a $C_3$ splitter.

20. The process as claimed in claim 11, wherein a mixture of propene and propane obtained in the bottoms from a column after the distillation in step (ii) is separated into propene and propane in a $C_3$ splitter.

21. The process as claimed in claim 12, wherein a mixture of propene and propane obtained in the bottoms from a column after the distillation in step (ii) is separated into propene and propane in a $C_3$ splitter.

22. The process as claimed in claim 10, wherein a mixture of propene and propane obtained in the bottoms from a column after the distillation in step (ii) is separated into propene and propane in a $C_3$ splitter.

23. The process as claimed in claim 15, wherein a mixture of propene and propane obtained in the bottoms from a column after the distillation in step (ii) is separated into propene and propane in a $C_3$ splitter.

24. The process as claimed in claim 16, wherein a mixture of propene and propane obtained in the bottoms from a column after the distillation in step (ii) is separated into propene and propane in a $C_3$ splitter.

25. An apparatus for carrying out a process according to claim 19, which comprises at least one reactor for preparing propene oxide, at least one apparatus for compressing the offgas stream, at least one distillation column for separating propene and propane from the offgas stream and a $C_3$ splitter for separating propene and propane.

26. A process for the continuous recirculation of an olefin which has not been reacted in the epoxidation of the olefin by means of hydroperoxide to give oxiranes and is present in an offgas stream formed during the epoxidation, comprising:
(i) compressing and cooling the offgas stream,
(ii) separating the olefin from the offgas stream obtained in step (i) by distillation,
(iii) epoxidizing the olefin separated off in step (ii) by means of hydroperoxide, wherein, in step (i), the offgas stream is compressed to a pressure of from 2 to 30 bar, cooled to from 0 to 70° C., and
wherein compression occurs in at least two stages in step (i), and
the offgas stream comprises unreacted olefin and oxygen.

27. The process according to claim 26, wherein the olefin is propene and the offgas stream further comprises propane.

28. A process for the continuous recirculation of an olefin which has not been reacted in the epoxidation of olefins by means of hydroperoxide to give oxiranes and is present in the offgas stream formed during the epoxidation, comprising:
(i) compressing and cooling the offgas stream,
(ii) separating the olefin from the offgas stream obtained in step (i) by distillation,
(iii) epoxidizing the olefin separated off in step (ii) by means of hydroperoxide, wherein the olefin is propene,
the offgas stream further comprises propane,
in step (i), the offgas stream is compressed to a pressure of from 12 to 20 bar,
cooled to from 30 to 40° C., and the offgas stream comprises unreacted olefin and oxygen.

29. A process for the continuous recirculation of propene which has not been reacted in the epoxidation of propene by means of hydroperoxide to give propene oxide and is present in an offgas stream formed during the epoxidation, comprising:
(i) compressing and cooling the offgas stream,
(ii) separating propene from the offgas stream obtained in step (i) by distillation,
(iii) epoxidizing the propene by means of hydroperoxide, wherein the offgas stream comprises propene, propane and oxygen, and
wherein
in step (i), the offgas stream is cooled to from 30 to 40° C. and compressed to a pressure of from 12 to 20 bar,
a mixture of propene and propane is obtained in bottoms from a column after distillation in step (ii), and
said mixture is separated into propene and propane in a $C_3$ splitter.

* * * * *